United States Patent [19]

Friedman

[11] Patent Number: 4,500,296
[45] Date of Patent: Feb. 19, 1985

[54] METHOD AND APPARATUS FOR REINFORCING DENTAL ANCHORS

[75] Inventor: Abraham Friedman, Brooklyn, N.Y.

[73] Assignee: IPCO Corporation, White Plains, N.Y.

[21] Appl. No.: 504,936

[22] Filed: Jun. 16, 1983

[51] Int. Cl.³ .............................................. A61C 5/04
[52] U.S. Cl. ..................................... 433/225; 433/215
[58] Field of Search .............. 433/225, 215, 165, 141, 433/3, 4

[56] References Cited

U.S. PATENT DOCUMENTS

| | | | |
|---|---|---|---|
| 2,682,063 | 6/1954 | Miloche | 433/3 |
| 3,083,463 | 4/1963 | Brooks et al. | 433/165 |
| 3,085,339 | 4/1963 | Wolfe | 433/4 |
| 3,229,727 | 1/1966 | Kenlon | 433/3 |
| 3,368,279 | 2/1968 | Weissman | 433/128 |
| 3,369,298 | 2/1968 | Weissman et al. | 433/128 |
| 3,434,209 | 3/1969 | Weissman | 433/225 |
| 3,534,476 | 10/1970 | Winters | 433/165 |
| 3,675,329 | 7/1972 | Weissman | 433/225 |
| 4,234,309 | 11/1980 | Sellers | 433/225 |
| 4,332,563 | 6/1982 | Weissman | 433/225 |

FOREIGN PATENT DOCUMENTS

| | | | |
|---|---|---|---|
| 1194061 | 11/1959 | France | 433/165 |
| 853645 | 11/1960 | United Kingdom | 433/165 |

*Primary Examiner*—John J. Wilson
*Attorney, Agent, or Firm*—Goodman & Teitelbaum

[57] ABSTRACT

A dental tool for wire wrapping a portion of a dental anchor projecting from dentition, the dental tool including an elongated rod with a cylindrical receiving chamber axially extending into the rod from a forward end thereof for receiving the projecting dental anchor therein. An elongated passageway extends through the rod offset from the chamber for receiving a supply of wire therethrough. A manipulating device is coupled to the rear end of the rod for rotation of the tool to thereby helically wrap the wire about the anchor for reinforcing the anchor. The wire can be extended from one dental anchor to an adjacent dental anchor to thereby splint the anchors together.

20 Claims, 17 Drawing Figures

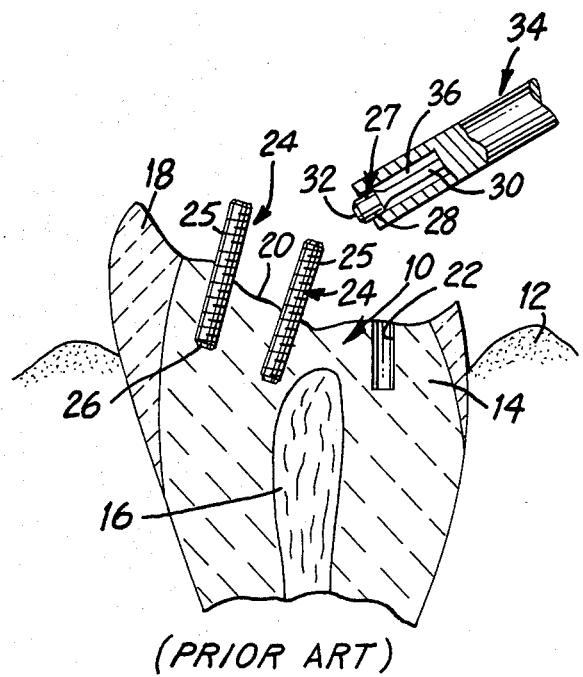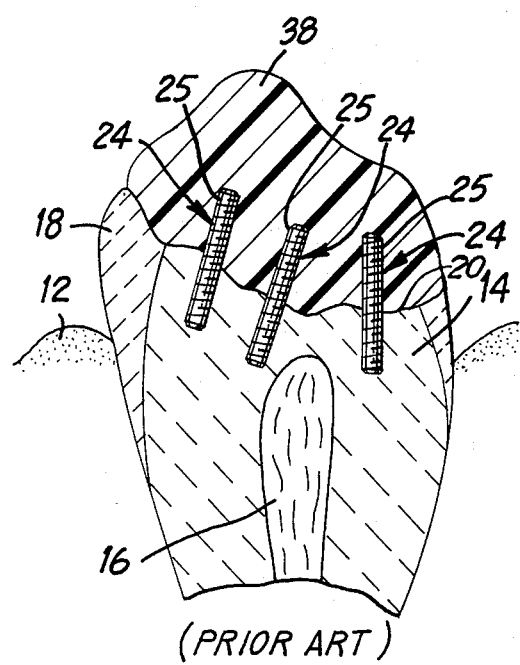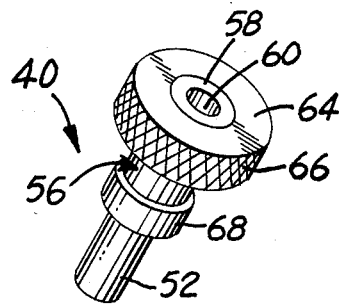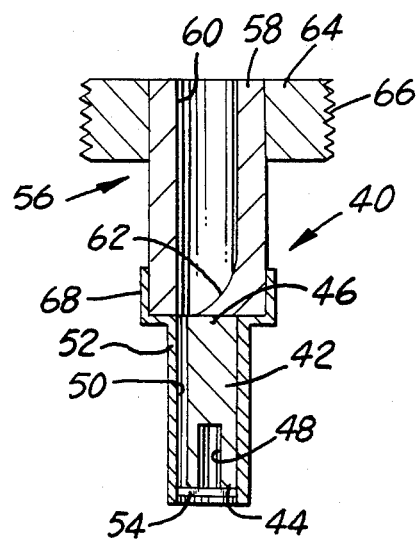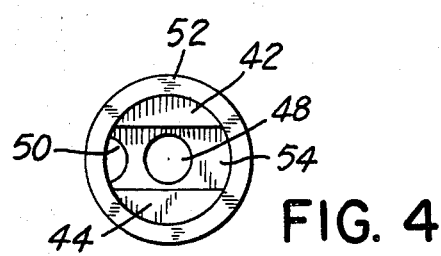
FIG. 1 (PRIOR ART)
FIG. 2 (PRIOR ART)
FIG. 3
FIG. 4
FIG. 5

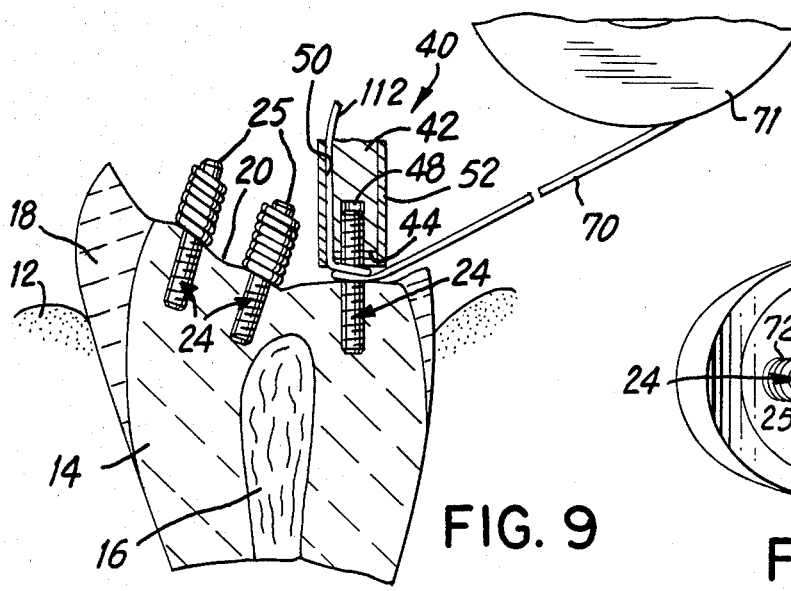

METHOD AND APPARATUS FOR REINFORCING DENTAL ANCHORS

BACKGROUND OF THE INVENTION

This invention relates to dental anchors for retaining a superstructure on broken or undermined dentition, and more particularly, to a method and apparatus for reinforcing and/or splinting together such dental anchors in order to improve their strength and retention ability.

When a tooth becomes broken or undermined, a common dental procedure is to build a superstructure onto the tooth stub. The procedure involves initially cutting down or suitably preparing the tooth stub, and then inserting one or more dental anchors into the tooth stub. The anchors generally comprise an elongate member having an anchoring portion at one end for securement within the tooth stub, with the other end projecting from the tooth stub. A superstructure is built onto the projecting end portion, thus being retained in place by securement to projecting end portion of the dental anchor.

Numerous dental anchors are presently available, as for example, described in U.S. Pat. Nos. 3,434,209 and 3,675,329, both assigned to the assignee of the present invention. In using dental anchors, it is generally desired to improve their strength as well as their retention capabilities for holding the superstructure thereon. An enlarged head may be formed on the projecting portion of the anchor in order to aid in the retention of the superstructure. Threads, grooves, or other types of channels are usually formed above the periphery of the dental anchors, to further improve its retention capabilities. Further improvement can be achieved by enlarging the anchor, however this would provide increased difficulty in inserting the anchor into the tooth stub.

Another dental procedure may require the splinting together of adjacent teeth. Various dental splints are presently available for this purpose. Normally, a channel is formed between the adjacent teeth and a suitable splint inserted within the channel. While the available splints are generally quite useful, nevertheless, it would be helpful if standard dental anchors could also be utilized in a splinting arrangement between adjacent dentition.

SUMMARY OF THE INVENTION

Accordingly, it is an object of the present invention to provide an apparatus for reinforcing a dental anchor projecting from a tooth stub.

Another object of the present invention is to provide an apparatus for wire wrapping the projecting portion of a dental anchor in order to increase its size, reinforce it, and improve its retention capabilities.

Still a further object of the present invention is to provide an apparatus for interconnecting a plurality of dental anchors projecting from one or more tooth stubs in a "daisy chain" arrangement, in order to interconnect the dental anchors and thereby improve their retention capabilities, strengthening them, and assisting in the formation of a superstructure onto the dentition.

Yet a further object of the present invention is to provide an apparatus for wire wrapping dental anchors in adjacent tooth stubs in order to splint the tooth stubs together.

Another object of the present invention is to provide a wire wrapping apparatus for a dental anchor in order to increase the size of the dental anchor to thereby improve its use in the formation of a dental superstructure.

A further object of the present invention is to provide a wire wrapping dental tool which can be driven by a hand peice in order to wire wrap a dental anchor to thereby reinforce it.

Yet another object of the present invention is to provide a method of improving the use of a dental anchor by wire wrapping the projecting portion of the dental anchor so as to enlarge it, reinforce it, and increase its retention capabilities.

A further object of the present invention is to provide a method of splinting together adjacent tooth stubs by inserting dental anchors in the dentition and splinting them together by means of wire which is being utilized for the wire wrapping of the dental anchors.

These objects are achieved in accordance with a preferred embodiment of the present invention, wherein there is provide a dental tool for reinforcing a dental anchor by means of wire wrapping the anchor portion projecting from the dentition. The dental tool includes an elongated cylindrical rod with a cylindrical receiving chamber axially extending into the rod from a forward end thereof in order to receive the projecting portion of the dental anchor. An elongated passageway extends through the rod, offset from the chamber, for receiving a supply of wire therethrough. A manipulating device is connected to the rear end of the rod for rotation of the tool in order to helically wrap the wire about the anchor, thereby reinforcing the anchor.

In one embodiment of the present invention, the manipulating device is a hand held handle coupled to the rear end of the cylindical rod. In another embodiment of the present invention, the manipulating device includes suitable apparatus for utilizing the dental tool in conjunction with an automatic hand piece, whereby the hand piece drives the dental tool to automatically wire wrap the projecting portion of the dental anchor.

The present invention also contemplates the combination of a dental anchor and the dental tool for the wire wrapping of the anchor. The anchor includes an elongated body having a securing anchoring portion for operative association within the tooth channel, and an extended portion protruding from the tooth channel. The dental tool wire wraps the periphery of the extending portion of the dental anchor.

The present invention also contemplates a method of building a superstructure on a tooth including the step of inserting a dental anchor into a tooth stub so that a portion of the anchor extends from the tooth surface. The extending portion is wire wrapped to enlarge and reinforce it. A superstructure is then built onto the tooth stub about the extending portion of the anchor.

The present invention also contemplates a method of splinting together at least two sections of the dentition by first forming a channel spanning across the sections to be splinted. At least one dental anchor is then inserted into each section of dentition with a portion of each anchor extending from the dentition into the channel. The extending portions of the dental anchors are wire wrapped, where the wire also interconnects the various anchors by having it pass from one anchor to another anchor during the course of the wire wrapping operation.

BRIEF DESCRIPTION OF THE DRAWINGS

Other objects and many of the attendant advantages of the present invention will be readily appreciated and better understood by reference to the following detailed description, when considered in connection with the accompanying drawings, in which like reference characters designate like parts throughout the figures thereof, and wherein:

FIG. 1 is a cross sectional view of a tooth or dentition with its surface excavated prior to building a superstructure thereon, and including the insertion of dental anchors into the dentition, in accordance with the prior art;

FIG. 2 is a cross sectional view similar to that shown in FIG. 1, showing the completed tooth with the superstructure built onto the tooth stub, in accordance with the prior art;

FIG. 3 is a perspective view of a dental tool, in accordance with the present invention, for use in wire wrapping the portion of a dental anchor projecting from the dentition;

FIG. 4 is a bottom plan view of FIG. 3, showing only the forward end of the dental tool;

FIG. 5 is an elevational, cross sectional view of the dental tool shown in FIG. 3;

FIG. 9 is a cross sectional view similar to that shown in FIG. 6, spowing an alternate method of utilizing the dental tool of the present invention for wire wrapping the individual dental anchors;

FIG. 10 is a top plan view of the wire wrapping arrangement shown in FIG. 6;

FIG. 11 is a top plan view of the wire wrapping and interconnecting arrangement shown in FIG. 7;

FIG. 12 is a top plan view of the wire wrapping and splinting arrangement shown in FIG. 8;

FIG. 13 is a partially cut-away side view of a hand piece having a dental tool inserted therein for use in the wire wrapping of dental anchors;

FIG. 14 is a top plan view taken along line 14—14 of FIG. 13, showing the latching arrangement of the hand piece;

FIG. 15 is a side elevational view of a dental tool for wire wrapping, which dental tool can be utilized in conjunction with the hand piece shown in FIG. 13;

FIG. 16 is a top plan view of the dental tool shown in FIG. 15; and

FIG. 17 is an exploded perspective view of an alternate embodiment of a dental tool for the wire wrapping of dental anchors, in accordance with the present invention.

DETAILED DESCRIPTION OF THE PREFERRED EMBODIMENTS

Figures 6, 7:
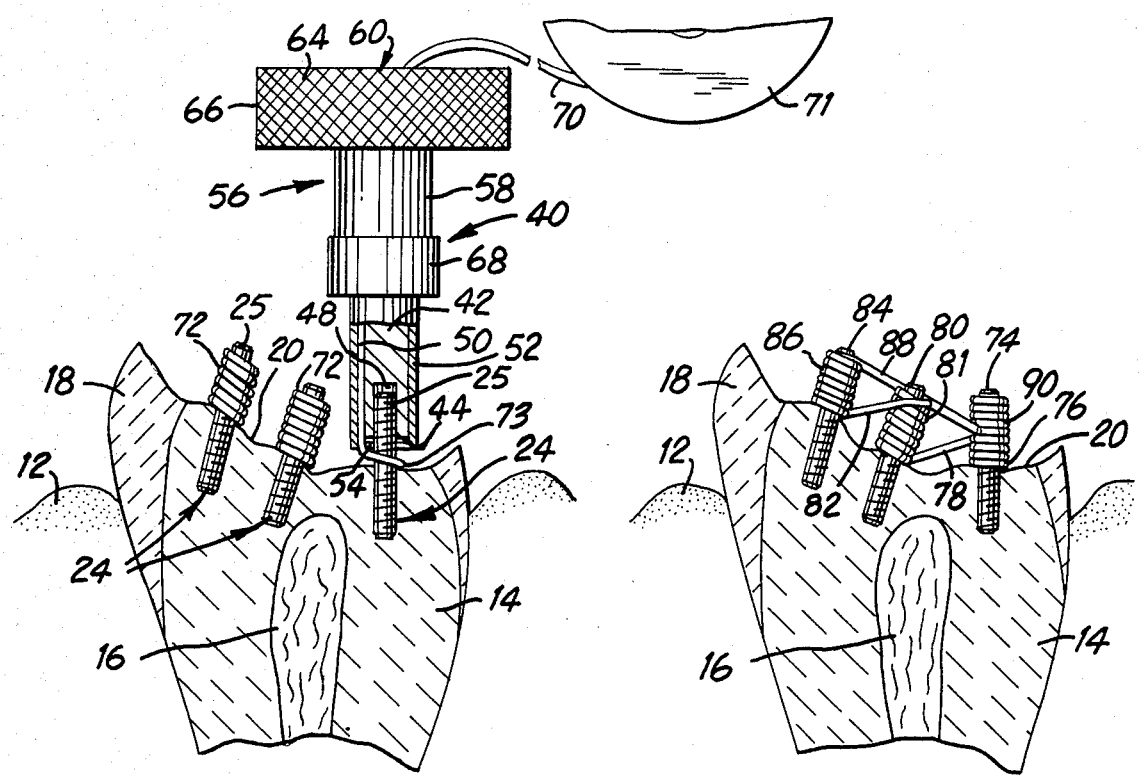
FIG. 6 is a cross sectional view of a tooth, similar to that shown in FIG. 1, showing the wire wrapping of each individual dental anchor in order to reinforce them.
FIG. 7 is a cross sectional view of a tooth, similar to that shown in FIG. 6, showing the wire wrapping of the individual dental anchors as well as the interconnection of the dental anchors in order to splint them together in a "daisy chain" arrangement.

Referring now to FIG. 1, there is shown a tooth or dentition 10 in the soft tissue or gingiva 12 of the human gum. As is well known to those skilled in the art, the body 14 of the tooth 10 is formed of dentin and encloses a pulp channel 16. The dentin projecting from the gingiva is covered by a layer 18 of enamel. In order to prepare the dentition for building a superstructure thereon, the tooth is excavated in order to remove the decay and undermined understructure so as to provide the excavated surface 20 with the decay removed. Any required root canal work may be accomplished at this time.

The first step in providing a superstructure is to form a plurality of channels 22 extending into the dentin 14 from the uncovered excavated surface 20. For this purpose, a standard spiral drill can be urged into the dentin in a conventional manner. The number of non-parallel channels 22 will depend upon the size and depth of the excavation. Normally, the various channels are drilled so as not to enter the pulp channel 16.

The next step in the process involves insertion of the dental anchors 24 into each of the channels 22. The dental anchors 24 are typically elongated cylindrical rods with peripheral threads or grooves thereabout. In some cases, the threads provide for self-threading of the rods into the channels. Normally, the lower end of the anchors 24 will contain a bevel 26 and the upper end is provided with a manipulating end 27. The manipulating end may typically include a cylindrical guide portion 28 and an elongated retaining portion 30. A narrow neck 32 interconnects the guide portion 28 to the dental anchors 24 to provide for the breaking away of the manipulating portion 28 after the dental anchor 24 has been suitably inserted into the channel 22. An upper portion 25 of the anchor extends above the excavated surface 20.

An appropriate tool 34 can be utilized for the insertion of the dental anchors 24 into the channels 22. The tool can be a chuck attachment to a hand piece, or it can be a manual drive device for manually inserting the dental anchors. The tool 34 includes an axially extending receiving chamber 36 for receiving the retaining portion 30 and the cylindrical guide portion 28 of the manipulating end therein.

When the dental anchor 24 has been appropriately seated into the channel 22, the tool 34 is utilized to snap off the manipulating end 27 from the dental anchor 24 so as to retain the dental anchor 24 properly seated into the tooth stub 10 with the upper portion 25 projecting therefrom.

With all of the dental anchors 24 inserted, a superstructure formed of any suitable material, may be constructed. The method of preparing and securing the superstructure can be done in accordance with conventional arrangements well known in the dental art. The superstructure is retained on the excavated tooth stub by means of the projecting portion of the dental anchors.

Although the aforedescribed method of securing a superstructure onto a tooth or dentition has been quite useful, there is continuously needed improved methods of reinforcing the dental anchors to be sure that they do not break, snap off, or are weakened during the process of forming the superstructure or during the patient's normal use of the superstructure. Although it might be suggested to utilize thicker dental anchors, in doing so there would also be required that a larger channel be drilled into the tooth stub, which would weaken the existing dentition. It is therefore desirable to reinforce the projecting portion of the dental anchor without necessarily reinforcing that portion of the dental anchor which is inserted into the tooth stub.

In some prior art arrangements, an additional wider head is provided on the projecting portion of the anchor in order to increase its retention capabilities. In some cases, the projecting portions are bent over. However, in each of these arrangements, the manufacturing complexity and cost of the dental anchor is increased, and the additional manipulation involved in the handling of the dental anchor is also increased.

Furthermore, although the prior art dental anchors shown in FIGS. 1 and 2 are separated, one method of improving the retention capabilities of the anchors would be to interconnect them in a splint-type of arrangement. This would improve the retention capabilities of the anchors and, at the same time, provide for reinforcement of the anchors. The inter-connecting splint arrangement could also be used when splinting together adjacent tooth stubs in connection with the building of artificial crowns or dental work spanning across a plurality of tooth stubs.

Referring now to FIGS. 3–5, there is shown one embodiment of a dental tool which can be utilized for the wire wrapping of the dental anchors in order to reinforce them, and at the same time, improve their retention capabilities. This tool can also be utilized for splinting together adjacent dental anchors.

The dental tool of the present invention is shown generally at 40, and comprises an elongated cylindrical rod 42 having a forward end 44 and a rear end 46. A cylindrical receiving chamber 48 axially extends into the rod from the forward end 44. An elongated passageway 50 is provided through the entire length of the cylindrical rod 42 in an offset relationship with respect to the axially extending receiving chamber 48. For convenience of manufacture, the passageway 50 is formed by cutting an elongated groove into the periphery of the rod 42, and then surrounding the rod 42 with a peripheral sleeve 52 to thereby provide the passageway 50 therebetween. A recess 54 is provided at least between the receiving chamber 48 and the passageway 50 at the free end of the rod 42. As best shown in FIG. 4, the recess 54 is an open transverse channel formed into forward end 44, extending entirely across the diameter of the forward end.

At the rear end 46, there is provided a manipulating handle 56 including a tubular member 58 having an axial channel 60 extending therethrough. At the lower end of the channel 60, there is found a sloped or funnel shaped wall section 62 in direct communication with the passageway 50, as shown in FIG. 5. An enlarged head 64, having a peripheral knurled edge 66, is provided about the upper end of the tube 58 in order for the user thereof to grasp and rotate the tool. The tubular member 58 is secured to the rear end 46 of the rod 42. The sleeve 52 terminates in an enlarged cup shaped section 68 in which the lower end of the tube 58 can snugly fit in a second arrangement.

Utilization of the tool 40 is best shown in FIGS. 6 and 10. Suitable wire 70 is provided from a conventional wire supply 71, such as a spool, and is fed into the axial channel 60 provided in the handle 56 and is fed along the sloped surface 62 so as to be fed into the elongated passageway 50 in the rod 42. The wire end 73 passes out from the forward end 44 of the tool 40. The extending portion 25 of the dental anchor 24 is then inserted into the axial receiving chamber 48. The end 73 of the wire 70 is retained, and the tool 40 is rotated about the anchor 24 so that the wire 70 from the supply 71 feeds down through the passageways 60, 50, and helically wraps about the extending portion 25 of the dental anchor 24. This provides for a wire wrap 72 about the extending portions 25, as shown in FIGS. 6 and 10.

The wire wrap 72 serves to reinforce the extending portion 25 of the dental anchor 24, and also serves to enlarge it. In this manner, greater strength is provided to the anchor 24. Furthermore, by enlarging the extending portion 25, there is effectively provided an enlarged head which increases the retention capabilities of the dental anchor 24 within the superstructure built onto the excavated tooth stub.

In addition to wire wrapping each dental anchor 24 individually, as was shown in FIGS. 6 and 10, during the course of the wire wrapping operation, the wire 70 can be extended from one dental anchor to the next dental anchor in order to splint the two anchors together, as shown in FIGS. 7 and 11. More particularly, there is shown a right most dental anchor 74, which has a lower part of its extension wire wrapped to form the wire wrapping 76 extending up to a central part thereof. A section 78 of the wire 70 then extends to the central dental anchor 80, where the wire wrapping begins at the bottom thereof and extends up to the top forming a wire wrap 81. The wire section 82 then extends from the top of the central dental anchor 80 to the left most dental anchor 84, which is then wire wrapped from the bottom thereof to produce the wrapping 86. Wire section 88 then extends from the top of the anchor 84 back to the middle of the first anchor 74, and then continues from the central part thereof upwardly to complete the wire wrapping, forming the upper wire wrap 90 thereon.

It should therefore be appreciated from FIGS. 7 and 11, that various types of wire wrapping arrangements can be made so as to interconnect one or more of a plurality of dental anchors in various interconnecting arrangements. The wire wrapping of the individual anchors serves to enlarge, reinforce and strengthen the anchor, and improve its individual retention capabilities. At the same time, by interconnecting the various dental anchors in a splinting arrangement, there is provided even further improvement in the retention capabilities thereof, and further reinforcement of the anchors. The type of interconnection shown in FIGS. 7 and 11 is typically referred to as a "daisy chain" interconnection.

Figure 8:
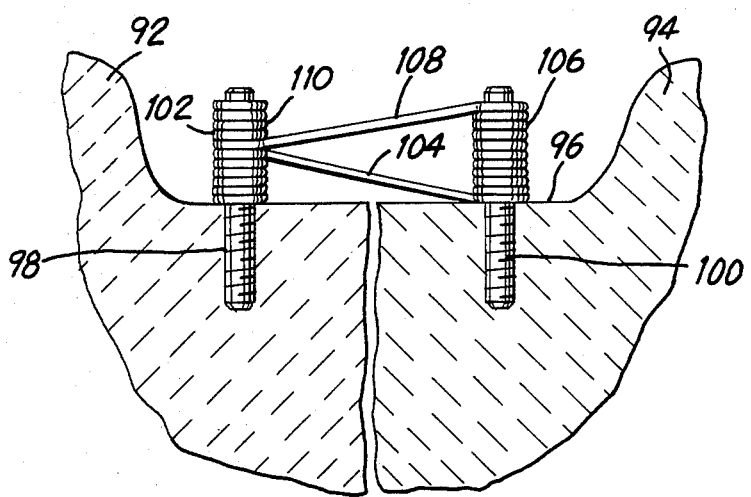
FIG. 8 is a cross sectional view of adjacent tooth stubs with dental anchors secured in the dentition, and utilizing the wire wrapping and the interconnecting of the dental anchors in order to provide a splinting arrangement between the adjacent tooth stubs.

Referring now to FIGS. 8 and 12, there is shown another use of the wire wrapping and the interconnecting arrangement, wherein adjacent tooth stubs are to be splinted together. More particularly, there is shown a first tooth stub 92 adjacent a second tooth stub 94. A recessed channel 96 is formed therebetween. In each of the tooth stubs, there is inserted a respective dental anchor 98, 100. Although only two anchors are shown, it should be understood that a plurality of individual anchors could be provided in each tooth stub and, furthermore, more than two such tooth stubs could also be involved. The individual anchors include a portion thereof which is threaded into the respective tooth stub, with another portion thereof projecting above the excavated surface into the channel 96. The dental anchor 98 has its projecting portion wire wrapped, in the above mentioned manner, with a lower wire wrap section 102 until it reaches approximately the mid point thereof. A wire section 104 then extends to the bottom of the projecting portion of dental anchor 100, and proceeds upward to wire wrap that anchor forming the wire wrap section 106. Upon reaching the top, a wire 108 extends back to the original anchor 98, and continues in the upper wire wrap section 110 to complete the wire wrapping of dental anchor 98.

Although a particular wire wrap arrangement has been shown, it should be understood that numerous other types of wire wrapping and interconnecting arrangements could be utilized in order to individually wire wrap each of the dental anchors, and at the same time interconnect the various wire wraps on the dental anchors by means of one or more wire sections.

Utilizing the arrangements shown in FIGS. 8 and 12, the dental anchors, in conjunction with the wire wrapping, can be used as a typical prior art splint in order to join together adjacent dentition. Appropriate dental superstructures could then be built onto the dentition and retained in place by means of the splint formed by the wire wrapped dental anchors.

Referring now to FIG. 9, an alternate method of utilizing the dental tool 40 is shown. Heretofore, as was shown in FIG. 6, the wire supply passed through the rear end of the tool 40 and extended downwardly through the entire length of the passageway 50 to project from the forward end 44 thereof. Utilizing that type of arrangement, the wire 70 which wraps each individual dental anchor 24 comes directly from the wire supply 71. In FIG. 9, it is noted that the wire 70 from the wire supply 71 does not pass downwardly through the handle, but on the other hand, has an end 112 thereof extending upwardly from the forward end 44 of the tool 40. A sufficient length of wire end 112 is inserted into the passageway 50 to permit the wire wrapping of the individual anchors 24. The projecting portion 25 of the dental anchor 24 is then inserted into the receiving chamber 48 of the rod 42 and the tool 40 is rotated. This time, the wire end 112 will wrap around the projecting portion 25 of the dental anchor 24. The wire 70 from the wire supply 71 is held during the operation to anchor that portion while the wire end 112 wraps around the dental anchor. With the arrangement shown in FIG. 9, each individual dental anchor can easily be separately wrapped. However, only the arrangement of FIG. 6 should be utilized when it is desired to also splint together adjacent dental anchors.

Although only one type of dental wire wrapping tool was shown in FIGS. 3-5, other embodiments of such a dental tool could also be utilized. For example, referring to FIGS. 15 and 16, there is shown a particular wire wrapping tool 114 which can be utilized in an automatically driven handpiece. The dental tool 114 includes an elongated rod 116 having an axial chamber 118 extending from the forward end 120 thereof. An elongated passageway 122 extends through the entire length of the rod 116 in an offset arrangement from the axially extending chamber 118, similar to the axial chamber 48 and elongated passageway 50 of rod 42 of the tool 40.

At the rear end 124, the tool 114 is shaped to facilitate its use within a handpiece. Although numerous types of arrangements can be provided for its coupling to the handpiece, the particular arrangement shown conforms to that heretofore described in U.S. Pat. Nos. 3,368,279 and 3,369,298, assigned to the assignee of the present invention. Appropriate coupling arrangements between dental tools and handpieces are explained in these prior art patents in more detail, and reference can be made to these patents for further explanations of the coupling arrangements. Briefly, the rear end 124 includes a stepped section 126 defining a vertical flat surface 128 and a horizontal shoulder 130. A reduced diameter neck portion 132 separates the main body portion from a head portion 134. It should be appreciated, that because of the stepped section 126, the passageway 122 is angularly curved within the tool so that it will extend axially from the rear end at an entry port 136.

The tool shown in FIGS. 15 and 16 can be utilized in the particular handpiece 138, shown in FIG. 13. The handpiece includes an arm 140 supporting a housing 142 in which extends a drive sleeve 144 terminating in a worm gear 146. The worm gear 146 drives a pinion gear 148 mounted onto a tubular rotor 150. The tool 114 is inserted into the tubular rotor 150 and driven thereby. Suitable ball bearings 154 facilitate rotation of the rotor within the housing 142.

At the upper end of the rotor 150, there is a ledge 156 extending inwardly into the central bore of the rotor 150. The shoulder 130 abuts against the ledge 156 thereby limiting the upward axial movement of the tool 114 within the rotor 150. At the same time, the forward edge of the ledge 156 terminates in a vertically flattened surface which mates against the flattened surface 128 on the tool 114 to drive the tool 114 as the rotor 150 rotates.

With the tool 114 inserted in the rotor 150 so that the shoulder 130 abuts the ledge 156, the reduced diameter neck portion 132 fits within a slot provided in the head 160 of the handpiece. As shown in FIGS. 13 and 14, a swinging arm 162 is pivoted within the head 160 by means of the screw 164 inserted into the head. The arm 162 includes the slot 166 which can grasp around the reduced neck portion 132, while still permitting the neck portion 132 to rotate therein. A manipulating handle 168 extends from the head 160 of the handpiece and serves to swing the arm 162 to vertically secure and release the tool 114 within the handpiece. The handle 168 snaps and locks onto the arm 140 of the handpiece 138 when the tool 114 is secured.

The enlarged head 134 of the tool extends to the top of the head 160, wherein an aperture 170 is provided to receive the head 134 and provide access to the port 136 in the tool 114. In this way, the wire 172 can pass through the aperture 170 in the head 160 of the handpiece and into the port 136 of the tool 114, then into the passageway 122, and exit from the forward end 120 to be wire wrapped about a dental anchor.

Utilizing the arrangement of FIGS. 13-15, the wire wrapping can be done automatically by driving the handpiece 138 and thereby rotating the dental tool 114 to wire wrap a dental anchor. The dental tool 114 can then be moved to an adjacent dental anchor to thereby splint together the two anchors, and further wire wrapping can now be carried out about the new anchor.

FIG. 17 shows yet a further embodiment of a wire wrapping dental tool, shown generally at 174. The tool includes an elongated rod 176, with a central chamber 178 axially extending from the forward end 180 for receiving the projected portion of a dental anchor. An elongated offset passageway is defined by means of the elongated slot 182 formed into the periphery of the tool. A notched section 184 is formed at the forward end of the tool to terminate the elongated passageway 182 in axially spaced arrangement from the forward end 180. A tubular sleeve 186 covers the forward notched end 184 permitting the wire to pass from the slot 182 to within the tubular sleeve 186 and then exit from the forward end. Both the tubular sleeve 186 as well as the bottom 188 of the rod 176 extend beyond the forward end 180 to effectively provide for the recess between the wire passageway 182 and the central axial chamber 178. Such recess is useful in extending the wire toward the dental anchor contained in the chamber 178 to thereby permit the initial turn of the wire to be directly formed upon the base of the tooth stub without any spacing therefrom.

It should be appreciated, that other tool arrangements for wire wrapping can be utilized in conjunction with the aforedescribed principles. The particular material from which the tool is made can be steel or other suitable dental material typically utilized for such tools. The wire itself can be metallic wire or other suitable wire useful for reinforcing dental anchors.

It should be understood of course that the foregoing disclosure relates to a preferred embodiment of the invention, and that it is intended to cover all changes and modifications of the example of the invention herein shown for the purpose of the disclosure, which modifications do not constitute departures from the spirit and scope of the invention.

What is claimed is:

1. In combination, a dental anchor for insertion into a channel formed in a tooth, and a dental tool coacting on the dental anchor, said dental anchor comprising an elongated body integrally including an anchoring portion for operative association within the channel and an extended portion protruding from said channel, said dental tool including means for wrapping a wire peripherally about at least a part of said extended portion of said dental anchor, said dental tool means including an elongated rod having an operating end and an opposite manipulating end, a receiving chamber provided in said rod and axially extending from said operating end for receiving said extended portion therein, a passageway provided longitudinally through said rod in an offset arrangement with said chamber for retaining a supply wire therein so that rotation of said tool helically wraps the wire about the extended portion of the dental anchor when said extended portion is received in said chamber, said dental tool being insertable into an automatically driven handpiece, a neck portion being provided on said manipulating end and having means for locking the tool into the handpiece, and a driving portion being provided on said tool for rotatably driving the tool by means of the handpiece.

2. A combination as in claim 1, wherein an axial bore is provided through said manipulating and in communication with said offset passageway, whereby said supply wire passes through said axial bore into said passageway.

3. A combination as in claim 2, wherein said axial bore terminates at its lower end in a sloped wall for directing the supply wire towards said passageway.

4. A combination as in claim 1, wherein said receiving chamber terminates at said operating end in an entry mouth, and said offset passageway terminates at said operating end in an entry port, and a recess is provided into the operating end of said rod, said recess extending between said entry mouth and said entry port.

5. A combination as in claim 1, wherein said passageway includes an elongated slot provided into the peripheray of said rod.

6. A combination as in claim 5, and comprising sleeve means for covering at least a portion of said rod for completing the passageway.

7. A method of building a superstructure on a tooth, comprising:
   insertion of a dental anchor into an excavated tooth so that a portion of the anchor projects outwardly from the tooth excavation;
   wire wrapping the projecting portion to enlarge and reinforce the projecting portion;
   said wire rapping comprising the steps of supplying wire through an offset longitudinal channel of a wire wrapping tool from its rear end such that the wire extends out of its forward end, inserting the dental anchor into an axial receiving chamber at the forward end of the wire wrapping tool, and retaining the extended end of the supply wire while rotating the wire wrapping tool to thereby wrap the supply wire about the dental anchor; and
   building a superstructure on the excavated tooth about the projecting portion.

8. A method as in claim 7, and comprising the steps of inserting a plurality of dental anchors into the excavated tooth, and interconnecting said dental anchors by extending the wrapping wire between the plurality of dental anchors during the wire wrapping operation to thereby splint together the dental anchors.

9. A method as in claim 8, and comprising the step of extending said wrapping wire from a top of one dental anchor to a bottom of another dental anchor.

10. A method as in claim 8, and comprising the step of extending the wrapping wire from a top of one dental anchor to a mid-section of another dental anchor.

11. A method as in claim 7, and comprising the steps of splinting together at least a second excavated tooth to the first mentioned excavated tooth, forming a channel spanning across the excavated teeth to be splinted, inserting at least one dental anchor into each excavated tooth with a portion of each anchor projecting from the excavated teeth into the channel, wire wrapping the projecting portion of each dental anchor, interconnecting the dental anchors together by passing the wire from one dental anchor to another dental anchor during the wire wrapping operation, and building a superstructure on each excavated tooth about the projecting portions and the wire wrappings.

12. A method of building superstructure on a tooth, comprising:
   insertion of a dental anchor into an excavated tooth so that a portion of the anchor projects outwardly the tooth excavation;
   wire wrapping the projecting portion to enlarge and reinforce the projecting portion;
   said wire wrapping comprising the steps of inserting an end portion of a wire supply into a forward end of an offset longitudinal passageway of a wire wrapping tool, inserting the dental anchor into an axial receiving chamber at a forward end of the wire wrapping tool, and rotating the wire wrapping tool to thereby wrap the inserted end portion of the wire about the dental anchor; and
   building a superstructure on the excavated tooth about the projecting portion.

13. A method as in claim 12, and comprising the steps of inserting a plurality of dental anchors into the excavated tooth, and interconnecting said dental anchors by extending the wrapping wire between the plurality of dental anchors during the wire wrapping operation to thereby splint together the dental anchors.

14. A method as in claim 13, and comprising the step of extending said wrapping wire from a top of one dental anchor to a bottom of another dental anchor.

15. A method as in claim 13, and comprising the step of extending the wrapping wire from a top of one dental anchor to a mid-section of another dental anchor.

16. A method as in claim 12, and comprising the steps of splinting together at least a second excavated tooth to the first mentioned excavated tooth, forming a channel spanning cross the excavated teeth to be splinted, inserting at least one dental anchor into each excavated tooth with a portion of each anchor projecting from the excavated teeth into the channel, wire wrapping the projecting portion of each dental anchor, inerconnecting the dental anchors together by passing the wire from one dental anchor to another dental anchor during the wire wrapping operation, and building a superstructure on each excavated tooth about the projecting portions and the wire wrappings.

17. A dental tool for wire wrapping a dental anchor projecting from dentition to thereby reinforce it, comprising an elongated rod, a receiving chamber axially extending into the rod from a forward end thereof for receiving the projecting dental achor, an elongated passageway extending through said rod offset from said chamber for receiving a supply of wire therein, manipulating means coupled to a rear end of said rod for rotation of said tool to helically wrap the wire about the anchor for reinforcing it, said manipulating means including engaging means for coupling said dental tool to an automatic handpiece for rotation thereof, said engaging means including a reduced neck portion adjacent said rear end for engagement by a gripping arm on the handpiece for axial retention in the handpiece, a flat wall provided on the rear end of the rod for engagement with a projecting ledge on a rotor of the handpiece for rotation therewith within the handpiece, and a transverse shoulder on said tool for abutting the ledge to suitably position the ledge and the flat into a cooperative arrangement.

18. A dental tool as in claim 17, wherein said manipulating means includes a channel in communication with said passageway, whereby an external supply of wire can pass through said channel into said passageway, and a sloped wall disposed between said channel and said passageway for feeding the supply of wire towards said passageway.

19. A dental tool as in claim 17, wherein said passageway extends axially through the rear of said tool to align with an aperture in a head portion of the handpiece to thereby receive the supply of wire exteriorly of the handpiece.

20. A dental tool as in claim 17, wherein said elongated passageway includes an elongated slot provided in a periphery of the rod, a notched forward end of said rod terminating said passageway in a spaced relationship from a mouth of said chamber, and sleeve means for covering said notched forward end.

* * * * *